United States Patent [19]

Iwata et al.

[11] Patent Number: 5,780,661
[45] Date of Patent: Jul. 14, 1998

[54] PROCESS FOR PREPARING ALLYLSILANE COMPOUND DERIVATIVES

[75] Inventors: Mitsuhiro Iwata, Saitama-ken; Hideki Sakurai, Miyagi-ken; Takanobu Sanji, Chiba-ken, all of Japan

[73] Assignee: Dow Corning Asia, Ltd., Tokyo, Japan

[21] Appl. No.: 869,697

[22] Filed: Jun. 5, 1997

[51] Int. Cl.$^6$ ................................................ C07F 7/08
[52] U.S. Cl. ........................... 556/429; 556/427; 556/488
[58] Field of Search ................................ 556/429, 427, 556/488

[56] References Cited

U.S. PATENT DOCUMENTS

| | | | |
|---|---|---|---|
| 3,686,326 | 8/1972 | Oswald et al. | 556/429 X |
| 3,859,360 | 1/1975 | Oswald et al. | 556/429 X |

OTHER PUBLICATIONS

Ojima, Iwao, "The hydrosilylation reaction," The Chmistry of Organic Silicon Compounds, 1989, pp. 1479–1527.
Colvin, Ernest, "Silicon Reagents in Organic Synthesis," Academic Press, 1988, pp. 21–49.
Mironov.V.F., "Orientation of addition of HBr and HI to allyl–and methallylsilane chlorides," Izvest. Akad. Nauk S.S.S.R., 1959 (10)1862 and abstracts.

*Primary Examiner*—Paul F. Shaver
*Attorney, Agent, or Firm*—Richard I. Gearhart

[57] ABSTRACT

Allyl silane compounds represented by the formula $(CH_2=CH-CH_2-)R_nSiCl_{3-n}$ (R represents, independently of each other, hydrocarbon groups with a carbon number of $C_1$ to $C_8$; n represents an integer from 0 to 3) are reacted with AX (AX stands for mercaptans, thiocarboxylic acids, carbon tetrachloride, or chloroform, the letter X represents, respectively, H bonded to sulfur in the case of mercaptans and thiocarboxylic acids, chlorine in the case of carbon tetrachloride, and H in the case of chloroform, and the letter A represents a residual group bonded to X) in the presence of radical generating agents, thereby obtaining allylsilane compounds represented by the formula $(ACH_2CHXCH_2)R_nSiCl_{3-n}$ (R, n, A and X have the same meaning as above).

4 Claims, No Drawings

PROCESS FOR PREPARING ALLYLSILANE COMPOUND DERIVATIVES

FIELD OF THE INVENTION

The present invention relates to novel allylsilane compound derivatives and a process for producing same. Allylsilane compound derivatives are industrially important as raw materials for functional polysilanes, raw materials for functional silicones, raw materials for functional silicone resins, or functional silane coupling agents.

DESCRIPTION OF THE PRIOR ART

The following two processes are representative processes used for the preparation of silane compounds having functional organic groups. One of the processes employs functional organic unsaturated compounds and hydrosilane compounds as raw materials and makes use of the hydrosilylation reaction with platinum, organic peroxides and the like as catalysts. In order to use this process, it is necessary that 1) unsaturated compounds having the desired functional groups should be present; 2) the desired functional groups should not poison the catalysts used in the hydrosilylation reaction; 3) the desired functional groups should be stable under the conditions of the hydrosilylation reaction (for example, see I. Ojima, The Chemistry of Organosilicon compounds. Part II (Editors Patai and Rappoport), p. 1479, John Wiley & Sons, New York, 1989). Glycidoxypropyl-trimethoxysilane, methacryloxypropyl-trimethoxysilane, and 3-chloropropyltrichlorosilane are prepared based on this process by using, respectively, allylglycidyl ether and trimethoxysilane, allyl methacrylate and trimethoxysilane, allyl chloride and trichlorosilane as raw materials. The other process uses functional organic metal compounds represented by lithium reagents, Grignard reagents and the like to introduce functional organic groups into chlorosilane, alkoxysilane and other silicon compounds. In this case, it is necessary that the functional organic metal compounds having the desired functional groups should be stable, and the functional organic metal compounds should selectively react with the starting silicon compounds. Because the functional organic metal compounds used in this process are generally expensive, in many cases it is inapplicable to the preparation of general-purpose organic functional silicon compounds. Many allylsilane compounds and alkinylsilane compounds are prepared based on this process (for example, see E. W. Colvin, Silicon Reagents in Organic Synthesis, p. 39–p. 46, Academic Press, London, 1988).

An additional process, which is not in common use, is a process that employs organic silane compounds having modifiable organic groups as raw materials and makes use of reactions involving these organic groups. In this third process, it is vital that the reaction of modification of organic groups should proceed in a selective manner and other portions of the organic silane compounds should not be damaged under the reaction conditions. For example, N-trimethoxysilylpropyl-N,N,N-trimethylammonium can be prepared based on this process by using 3-chloropropyltrimethoxysilane and trimethylamine as raw materials.

Most functional silane compounds are commonly prepared based on the above described first or second process, and there are few examples of using the third process. This is due to the damage to the other portions of the starting organic silanes caused in many cases by the modification reaction when this process is used. However, if this process could be widely used, the types and number of the functional silanes that could be created would be greatly increased, which is why hopes have been pinned on the development of various industrial applications thereof to raw materials for functional silicon polymers and organic silane reagents.

On the other hand, allyl groups bonded to silicon in allyl functional silane compounds can be easily desilylated by using nucleophilic reagents, and for this reason, in many cases it is difficult to conduct selective chemical modification of allyl groups without damaging other portions, and there are few examples of such modification. An example of chemical modification of allyl groups of allylsilane compounds is given in a report describing a reaction of addition of HBr and HI in the presence of benzoyl peroxide (Iz. Akad. Nauk SSSR, Ser. Khim. (1959) (10) 1862).

OBJECTS OF THE INVENTION

It is an object of the present invention to provide a method for generating functional organic silicon compounds which are difficult to obtain by conventional methods. Another object is to obtain aforementioned compounds by catalytic addition reactions that involve allyl functional silanes. Still another object is to provide a method for obtaining aforementioned compounds by conducting catalytic chemical modifications of the double carbon-carbon bonds in allyl groups without causing desilylation.

These and other objects will become apparent after the consideration of the ensuing description with practical examples.

SUMMARY OF THE INVENTION

The present invention is a new and novel composition comprising $(ACH_2CHXCH_2)R_nSiCl_{3-n}$, where R is independently a saturated or unsaturated hydrocarbon group having from 1 to 8 carbon atoms, and n represents an integer from 0 to 3, X is either H or Cl, and A is YS, YC(=O)S, or $CCl_3$, where Y is a phenyl group or a saturated hydrocarbon group having from 1 to 8 carbon atoms. This compound is a result of the reaction product of (I) $(CH_2=CH—CH_2—)R_nSiCl_3$, and (II) AX, wherein R is independently a saturated or unsaturated hydrocarbon group having from 1 to 8 carbon atoms, and n represents an integer from 0 to 3, and AX is either a mercaptan, a thiocarbocylic acid, carbon tetrachloride or chloroform. The reaction takes place in the presence of a radical generating agent.

DETAILED DESCRIPTION OF THE INVENTION

The authors of the present invention have discovered a process, in which allylsilane compounds are reacted with specific substrates in the presence of free radical initiators to achieve a chemical modification of the allyl groups bonded to silicon. Because in this reaction the radicals produced by the free radical initiators act as catalysts for the addition reaction involving the allyl groups, they can be added in catalytic amounts relative to the substrate or the allylsilane compound.

The present invention is a process for preparing allylsilane compound derivatives, in which allyl silane compounds represented by the general formula (I) indicated below:

$$(CH_2=CH—CH_2—)R_nSiCl_{3-n} \qquad (1)$$

(in the formula, R represents, independently of each other, saturated or unsaturated hydrocarbon groups with a carbon number of 1 to 8, and n represents an integer from 0 to 3)

are reacted with special reaction substrates, (II) AX (where AX stands for mercaptans, thiocarboxylic acids, carbon tetrachloride, or chloroform, the letter X represents, respectively, a hydrogen atom bonded to sulfur in the case of mercaptans and thiocarboxylic acids, chlorine in the case of carbon tetrachloride, and a hydrogen atom in the case of chloroform, and the letter A represents a residual group bonded to X) in the presence of radical generating agents, with the derivatives, represented by the general formula indicated below (in the formula, R, n, A and X have the same meaning as above), having a structure in which the AX are added across the unsaturated bonds of allyl groups.

Mercaptans (YSH, A=YS, X=H, Y stands for a saturated hydrocarbon group with a carbon number of 1 to 8, or a phenyl group), thiocarboxylic acids (YC(=O)SH, A=YC(=O)S, X=H, Y stands for saturated hydrocarbon groups with a carbon number of 1 to 8 or a phenyl group), carbon tetrachloride ($CCl_4$, A=$CCl_3$, X=Cl), and chloroform ($CHCl_3$, A=$CCl_3$, X=H) can be cited as examples of the AX substrate that can be used in the present invention.

As for specific examples of mercaptans and thiocarboxylic acids, methyl mercaptan, ethyl mercaptan, n-propyl mercaptan, isopropyl mercaptan, n-butyl mercaptan, n-pentyl mercaptan, neopentyl mercaptan, n-hexyl mercaptan, n-heptyl mercaptan, n-octyl mercaptan, and thiophenol can be suggested as mercaptans, and thiolacetic acid, thiopropionic acid, thiohexanoic acid, and thiobenzoic acid can be suggested as thiocarboxylic acids. Among them, n-propyl mercaptan, thiophenol and thiolacetic acid are preferable.

Allyltrichlorosilane, allylmethyldichlorosilane, allyltrimethylsilane, allylethyldichlorosilane, allylmethylethylchlorosilane, allyldiethylchlorosilane, allylhexyldichlorosilane, allylphenyldichlorosilane, allyldiphenylchlorosilane, and allyltriephenylsilane can be cited as examples of allylsilane compounds. Among them, allylmethyldichlorosilane is preferable.

There are no particular limitations concerning the radical generating agents used in the present invention as long as their decomposition temperature is higher than room temperature and lower than the decomposition temperature of the products and reagents used in the present invention. However, diacyl peroxides represented by benzoyl peroxide, lauroyl peroxide, and chlorobenzoyl peroxide, dialkyl peroxides represented by di(t-butyl) peroxide, and azo compounds represented by azobisisobutylonitrile and azobiscyanopentanoic acid, are preferable from the standpoint of availability, safety of decomposition products and handling. The required amount of the added radical generating agents is in the range from 0.0001 to 0.1 in terms of mole ratio with respect to the substrate. However, from the standpoint of the rate of reaction and economic efficiency, it is preferable for the amount to be in the range from 0.001 to 0.01.

The present reaction can be conducted without a solvent, otherwise, the reaction can be conducted in a solvent by using a solvent that is highly stable with respect to the radical reaction in comparison with the substrate of the present reaction and does not react with the substrate, for example, saturated hydrocarbons, benzene and the like.

It is appropriate to conduct the reaction at a temperature of from 50° C. to 250° C., but it is preferable to conduct it at a temperature of from 60° C. to 80° C., provided that the reaction time is not too long, the reaction is easy to control, and the decomposition of the products does not occur. The produced allylsilane compounds with added functional groups can be separated from the reaction mixture directly by using distillation.

(Application Examples)

Below, the present invention is explained in detail by referring to application examples. However, the present invention is not limited to them.

In addition, $^1$H-nmr, $^{13}$C{$^1$H}-nmr, $^{29}$Si{$^1$H}-nmr in the descriptions of the characterization of the products in the examples shown below represent, respectively, proton nuclear magnetic resonance spectra, carbon-13 nuclear magnetic resonance spectra (proton decoupling), and silicon-29 nuclear magnetic resonance spectra (proton decoupling). $CDCl_3$ represents heavy chloroform. The letters s, d, t, m and br shown in the representation of the date of the proton nuclear magnetic resonance spectra represent, respectively, singlets, doublets, triplets, multiplets and broad peaks. 1H, 2H, 3H and the like mean, respectively, spectral intensity equivalent to 1, 2 and 3 protons. J designates the spin-spin coupling constant (unit: Hertz). As for the chemical shift of the nuclear magnetic resonance spectra, in proton NMR, it is a value obtained with chloroform at 7.24 ppm, in carbon-13 NMR, it is a value obtained with chloroform at 77 ppm, and in silicon-29 NMR, it is a value obtained using tetramethyl silane as an external standard and setting it to 0 ppm. GC-MS represents gas chromatography-mass spectrometry.

The allylsilane compounds used in the present application examples were commercially available compounds or compounds synthesized by using well-known methods.

Application Example 1

(Preparation of 3-(phenylthio) propyl (methyl) dichlorosilane)

26.8 g thiophenol, 18.8 g allyl (methyl) dichlorosilane and 0.60 mg azobisisobutylonitrile were put in a 100-mL three-neck flask that had been subjected to nitrogen substitution and the mixture was heated at 60° C. for 5 hours. After the reaction, the product was distilled under reduced pressure, obtaining 3-(thiophenyl) propyl (methyl) dichlorosilane with a 88% yield.

Analytic results: 3-(thiophenyl) propyl (methyl) dichlorosilane:

Colorless transparent liquid;

b. p 95°–97° C./0.05 mmHg;

MS (70 eV) m/e (%) 266 (19.9, M$^+$+2), 264 (27.4, M$^+$), 123 (100), 113 (71.4), 47 (54.3);

$^1$H-NMR ($CDCl_3$, δ), 0.76 (s, 3H), 1.25~1.35 (m, 2H), 1.90~1.95 (m, 2H), 2.98 (t, J=6.6 Hz, 2H), 7.30~7.40 (m, 5H);

$^{13}$C-NMR ($CDCl_3$, δ) 5.1, 20.6, 22.2, 36.1, 126.1, 128.9, 129.5, 135.9;

$^{29}$Si-NMR ($CDCl_3$, δ) 32.4.

Application Example 2

(Preparation of propyl (3-methyldichlorosilyl) propyl) sulfide)

26.4 g n-propyl mercaptan, 12.6 g allyldichloromethylsilane and 0.32 mg azobisisobutylonitrile were put in a 50-mL three-neck flask that had been subjected to nitrogen substitution and the mixture was heated at 60° C. for 4 hours. The product was distilled under reduced pressure, obtaining propyl (3-methyldichlorosilyl) propyl) sulfide with a 77% yield.

Analytic results: propyl (3-methyldichlorosilyl) propyl) sulfide:

Colorless transparent liquid;

b.p 63°–65° C./0.05 mmHg;

MS (70 ev) m/e (%) 232 (11.4, M$^+$+2), 230 (15.9, M$^+$), 113 (66.5), 89 (100);

$^1$H-NMR (CDCl$_3$, δ) 0.69 (s, 3H), 0.9 (t, J=7.5 Hz, 3H), 1.13~1.18 (m, 2H), 1.45~1.58 (m, 2H), 1.64~1.78 (m, 2H), 2.39 (t, J=7.5 Hz, 2H), 2.48 (t, J=7.0 Hz, 2H);

$^{13}$C-NMR (CDCl$_3$, δ) 5.0, 13.2, 20.5, 22.4, 22.7, 33.7, 34.1;

$^{29}$Si-NMR (CDCl$_3$, δ) 32.4.

Application Example 3

(Preparation of 3-(methyldichlorosilyl)propyl thioacetate)

26.9 g thioacetic acid, 18.4 g allyldichloromethylsilane and 0.31 mg azobisisobutylonitrile were put in a 500-mL three-neck flask that had been subjected to nitrogen substitution and the mixture was heated at 60° C. for 5 hours. The product was distilled under reduced pressure, obtaining 3-(methyldichlorosilyl)propyl thioacetate with a 81% yield.

Analytic results: 3-(methyldichlorosilyl)propyl thioacetate:

Red liquid;

b. p 68°–69° C./0.1 mmHg;

MS (70 ev) m/e (%) 232 (0.2, M$^+$+2), 230 (0.3, M$^+$), 152 (6.3), 113 (10.4), 45 (100);

$^1$H-NMR (CDCl$_3$, δ), 0.86 (s, 3H), 1.10~1.20 (m, 2H), 1.65~1.70 (m, 2H), 2.23 (s, 3H) 2.80~2.83 (m, 2H);

$^{13}$C-NMR (CDCl$_3$, δ) 4.8, 20.5, 22.7, 30.3, 30.9, 194, 8;

$^{29}$Si-NMR (CDCl$_3$, δ) 32.0.

Application Example 4

(Preparation of 2,4,4,4-tetrachlorobutyl (methyl) dichlorosilane)

30.7 g carbon tetrachloride, 7.7 g allyldichloromethylsilane and 0.96 mg benzoyl peroxide were put in a 500-mL three-neck flask that had been subjected to nitrogen substitution and the mixture was heated at 80° C. for 4 hours. The product was distilled under reduced pressure, obtaining 2,4,4,4-tetrachlorobutyl (methyl) dichlorosilane with a 54% yield.

Analytic results: 2,4,4,4-tetrachlorobutyl (methyl) dichlorosilane:

Colorless transparent liquid;

b. p 72°–73° C./0.05 mmHg;

MS (70 ev) m/e (%) 271 (0.6, M$^+$–35), 235 (2.9), 175 (28.1), 113 (100);

$^1$H-NMR (CDCl$_3$, δ), 0.88 (s, 3H), 1.81~2.01 (m, 2H), 3.11~3.34 (m, 2H), 4.48~4.56 (m, 1H);

$^{13}$C-NMR (CDCl$_3$, δ) 5.5, 31.9, 51.2, 62.2, 94.4;

$^{29}$Si-NMR (CDCl$_3$, δ) 28.3.

Application Example 5

(Preparation of 4,4,4-trichlorobutyl (methyl) dichlorosilane)

34.6 g chloroform, 4.72 g allyldichloromethylsilane and 0.65 mg benzoyl peroxide were put in a 50-mL three-neck flask that had been subjected to nitrogen substitution and the mixture was heated at 60° C. for 27 hours. The product was distilled under reduced pressure, obtaining 4,4,4-trichlorobutyl (methyl) dichlorosilane with a 24% yield.

Analytic results: 4,4,4-trichlorobutyl (methyl) dichlorosilane:

Colorless transparent liquid;

b. p 63°–65° C./0.05 mmHg;

MS (70 ev) m/e (%) 257 (1.2, M$^+$–15), 201 (5.9), 141 (24.4), 113 (100);

$^1$H-NMR (CDCl$_3$, δ), 0.61 (s, 3H), 1.00~1.06 (m, 2H), 1.76~1.82 (m, 2H), 2.52~2.57 (m, 2H);

$^{13}$C-NMR (CDCl$_3$, δ) 4.6, 19.2, 19.7, 56.5, 98.5;

$^{29}$Si-NMR (CDCl$_3$, δ) 31.8.

Thus it has been shown that the present invention makes possible the preparation of allylsilane compound derivatives that are industrially important as raw materials for functional polysilanes, raw materials for functional silicones, raw materials for functional silicone resins, or functional silane coupling agents with high selectivity and high efficiency by adding readily industrially available inorganic or organic substrates to the allyl groups of allyl functional silane compounds by using a reaction, in which radical generating agents are employed as catalysts.

What we claim is:

1. A composition comprising:

where R is independently a saturated or unsaturated hydrocarbon group having from 1 to 8 carbon atoms, and n represents an integer from 0 to 3, X is either H or Cl, and A is YS, YC(=O)S, or CCl$_3$, where Y is a phenyl group or a saturated hydrocarbon group having from 1 to 8 carbon atoms.

2. A composition comprising the reaction product of (I) (CH$_2$=CH—CH$_2$—)R$_n$SiCl$_{3-n}$ and (II) AX, wherein R is independently a saturated or unsaturated hydrocarbon group having from 1 to 8 carbon atoms, and n represents an integer from 0 to 3, and AX is either a mercaptan, a thiocarbocylic acid, carbon tetrachloride or chloroform.

3. The reaction product of claim 2, wherein the reaction takes place in the presence of a radical generating agent.

4. The reaction product of claim 1, in which the compounds represented by formula (I) are alkylmethyldichlorosilanes and the compounds represented by (II) are either PhSH, where Ph represents a phenyl group, C$_3$H$_7$SH, CH$_3$COSH, CCl$_4$ or CHCl$_3$.

* * * * *